(12) United States Patent
Thornton et al.

(10) Patent No.: US 9,265,889 B2
(45) Date of Patent: Feb. 23, 2016

(54) PREFILLED MEDICAL INJECTION DEVICE

(71) Applicants: Daniel W. Thornton, Englewood, CO (US); Mark Christian Johnson, Phoenix, AZ (US)

(72) Inventors: Daniel W. Thornton, Englewood, CO (US); Mark Christian Johnson, Phoenix, AZ (US)

(73) Assignee: Adar MedTech, Inc., Northridge, CA (US)

(*) Notice: Subject to any disclaimer, the term of this patent is extended or adjusted under 35 U.S.C. 154(b) by 152 days.

(21) Appl. No.: 14/052,167

(22) Filed: Oct. 11, 2013

(65) Prior Publication Data

US 2014/0323975 A1 Oct. 30, 2014

Related U.S. Application Data

(63) Continuation-in-part of application No. 13/870,815, filed on Apr. 25, 2013, and a continuation-in-part of application No. PCT/US2012/047531, filed on Jul. 20, 2012.

(60) Provisional application No. 61/638,059, filed on Apr. 25, 2012.

(51) Int. Cl.
*A61M 5/178* (2006.01)
*A61M 5/31* (2006.01)
*A61L 29/04* (2006.01)
*A61M 5/20* (2006.01)
*A61M 5/32* (2006.01)
(Continued)

(52) U.S. Cl.
CPC .............. *A61M 5/3135* (2013.01); *A61L 29/04* (2013.01); *A61M 5/2033* (2013.01); *A61M 5/282* (2013.01); *A61M 5/168* (2013.01); *A61M 5/2053* (2013.01); *A61M 5/288* (2013.01); *A61M 5/30* (2013.01); *A61M 5/3146* (2013.01); *A61M 5/3202* (2013.01); *A61M 2005/2073* (2013.01); *A61M 2005/312* (2013.01); *B29C 49/04* (2013.01); *B29C 2791/006* (2013.01); *B29L 2031/7544* (2013.01)

(58) Field of Classification Search
CPC ..................... A61M 2005/312; A61M 5/2033; A61M 5/2455
See application file for complete search history.

(56) References Cited

U.S. PATENT DOCUMENTS 3,989,045 A 11/1976 Van Eck
4,227,528 A * 10/1980 Wardlaw ....................... 604/139
(Continued)

OTHER PUBLICATIONS http://www.brevettiangela.com/index.php?option=com_content&view=article&id=50&Itemid=88&lang=en, Feb. 12, 2014.

*Primary Examiner* — Aarti B Berdichevsky
(74) *Attorney, Agent, or Firm* — Michael P. Mazza, LLC

(57) ABSTRACT

A prefilled medical injection device with production specific elements is provided as a single use disposable injection device that is optimally suited for mass production through the Blow Fill Seal manufacturing process. The device utilizes a valve and a needle assembly fused to an insert. The valve and the needle assembly are positioned within the insert forming a conduit. The needle assembly is covered with a needle cap that is detachably coupled to protecting the needle assembly from contamination and a user from accidental needle stick. The insert is engaged to the bellows during the BFS manufacturing process and hermetically sealed by a parison layer that covers exterior portion of the insert and the needle cap. The parison layer is formed and trimmed creating exterior features that facilitate the use of the prefilled medical injection.

14 Claims, 8 Drawing Sheets

(51) Int. Cl.

| | |
|---|---|
| A61M 5/168 | (2006.01) |
| A61M 5/28 | (2006.01) |
| A61M 5/30 | (2006.01) |
| B29L 31/00 | (2006.01) |
| B29C 49/04 | (2006.01) |

(56) References Cited

U.S. PATENT DOCUMENTS

| | | | |
|---|---|---|---|
| 4,342,184 A | | 8/1982 | Van Eck |
| 4,772,271 A | * | 9/1988 | Meyer et al. ............ 604/184 |
| 5,261,881 A | | 11/1993 | Riner |
| 5,538,506 A | | 7/1996 | Farris |
| 6,331,174 B1 | | 12/2001 | Reinhard |
| 6,383,166 B1 | | 5/2002 | Farris |
| 7,188,750 B2 | | 3/2007 | Vogel |
| 7,766,872 B2 | | 8/2010 | Ackerman |
| 7,892,211 B2 | * | 2/2011 | McCulloch et al. .......... 604/192 |
| 7,998,120 B2 | | 8/2011 | Sano |
| 8,043,267 B2 | | 10/2011 | Nanba |
| 8,226,630 B2 | | 7/2012 | Ackerman |
| 8,251,972 B2 | | 8/2012 | Consolaro |
| 8,562,564 B2 | | 10/2013 | Lesch |
| 2004/0267194 A1 | | 12/2004 | Sano |
| 2005/0182370 A1 | | 8/2005 | Hato |
| 2006/0032768 A1 | | 2/2006 | Hamai |
| 2007/0102850 A1 | | 5/2007 | Vogel |
| 2007/0270743 A1 | | 11/2007 | Ackerman |

\* cited by examiner

PREFILLED MEDICAL INJECTION DEVICE

The current application is a continuation in part of U.S. application Ser. No. 13/870,815 filed Apr. 25, 2013, which is a non-provisional of U.S. Provisional Application No. 61/638,059 filed Apr. 25, 2012. Further, the current application is a continuation in part of PCT Application Number PCT/US12/47531 filed Jul. 20, 2012, which claims benefit of U.S. Provisional Patent Application 61/638,059 filed Apr. 25, 2012.

FIELD OF THE INVENTION

The present invention relates generally to a prefilled medical injection device. More specifically, the invention relates to a prefilled, single-use, medical injection device particularly designed to be manufactured using a Blow-Fill-Seal process.

BACKGROUND OF THE INVENTION

There are pluralities of the hypodermic syringe type injection device. The vast majority of the devices are derivative of French physician Charles Pravaz' well-known design. The design consists of a cylinder body, a piston, and a hypodermic needle. This design works very well for introducing and extracting fluids from patients, and has been adapted recently as a prefilled delivery method made suitable by following specific pre-determined safety protocols that add significant cost to the infusion equation.

Prefilled medical injection devices provide health care workers with a more efficient way to administer medications. The ubiquitous hypodermic syringe has seen a multitude of incremental advancements and improvements over the years in order to deal with the myriad of problems hypodermic syringes present in its manufacture, distribution, storage and use. Many of these advancements are unique to the problems relating to the prefilled syringe, which creates many new challenges because of the prefilled format. For example, prefilled hypodermic syringes face problems relating to chemical interactions with silicone, a common lubricant that allows the plunger to move down the cylinder, as well as adhesives, rubber, and tungsten. Further, transportation presents additional problems relating to atmospheric changes, creating a potential for pressure increases inside the cylinder body causing the device to extrude medication, wasting medication, while decreases cause the device to suction up outside air, which increases the risk of contamination. Many other problems exist in their use, such as the accidental removal or dislodgement of the plunger, as well as the potential for needle stick injury depending upon the type of needle used. This has been a problem to many health care professionals and has forced them to switch back to the vial syringe method for delivering vaccinations.

Although, there are multitudes of prior arts that incorporate solutions to the above problem the majority of them still carry a major disadvantage. The majority of injection devices require that the device be uncapped and recapped to avoid sticking others with a contaminated needle. The requirement to recap a syringe has created a major risk factor for healthcare workers, accidentally pricking themselves with a soiled needle.

It is therefore an object of the present invention to introduce a device that is prefilled with medication, adjusts to changes in ambient temperature and pressure, while providing a risk reducing mechanism to inject patients. Additionally the invention is designed for a mass production method (Blow-Fill-Seal method) that minimizes the risk of contamination. Blow-Fill-Seal has numerous requirements and limitations and the ampoule and collar (insertion technology) have both been designed to be compatible with Blow-Fill-Seal manufacturing.

BRIEF DESCRIPTIONS OF THE DRAWINGS

DETAIL DESCRIPTIONS OF THE INVENTION

All illustrations of the drawings are for the purpose of describing selected versions of the present invention and are not intended to limit the scope of the present invention.

Figure 1:
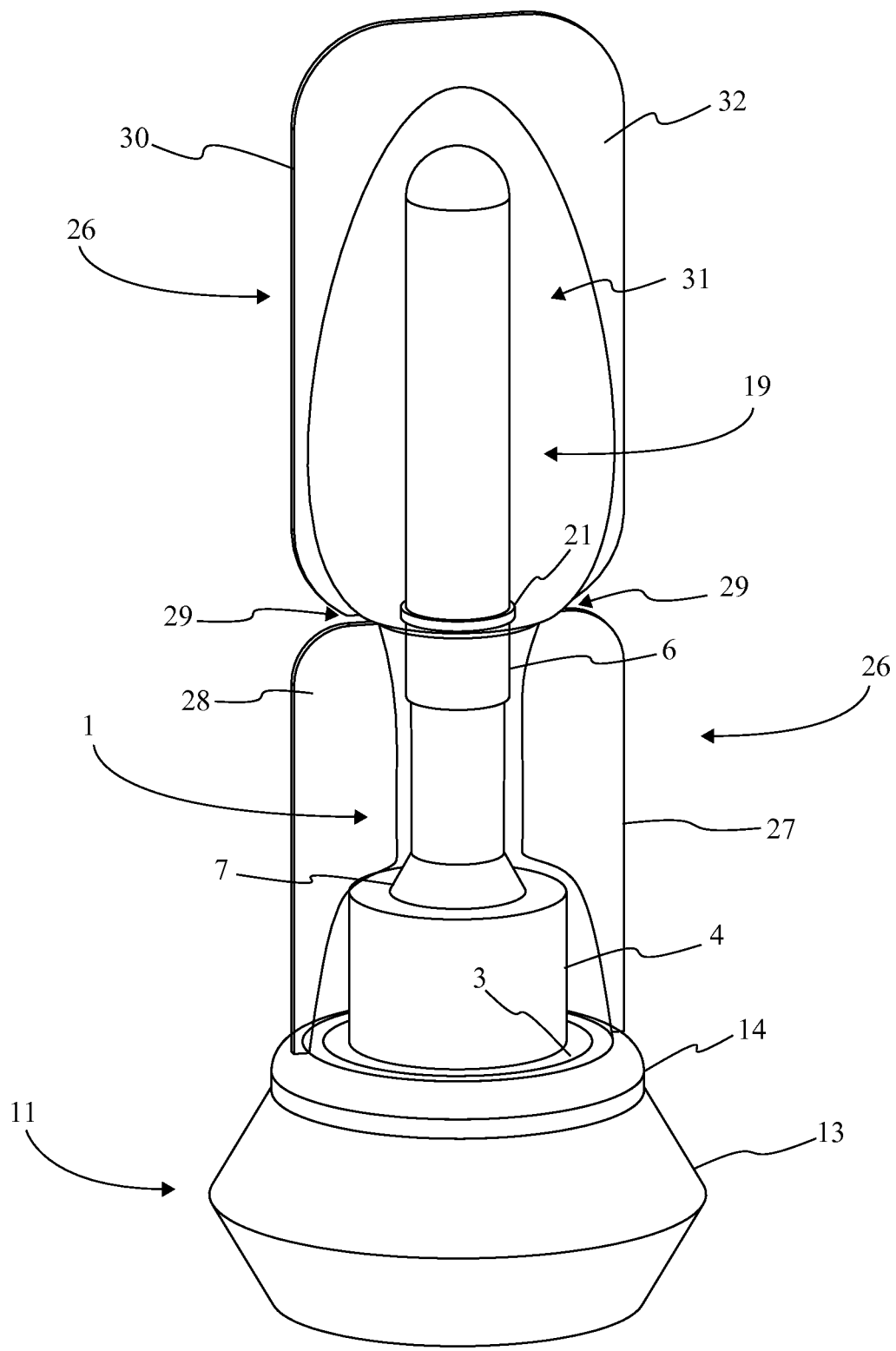
FIG. 1 is a perspective view displaying the prefilled medical injection device as per the current embodiment of the present invention.
Figure 2:
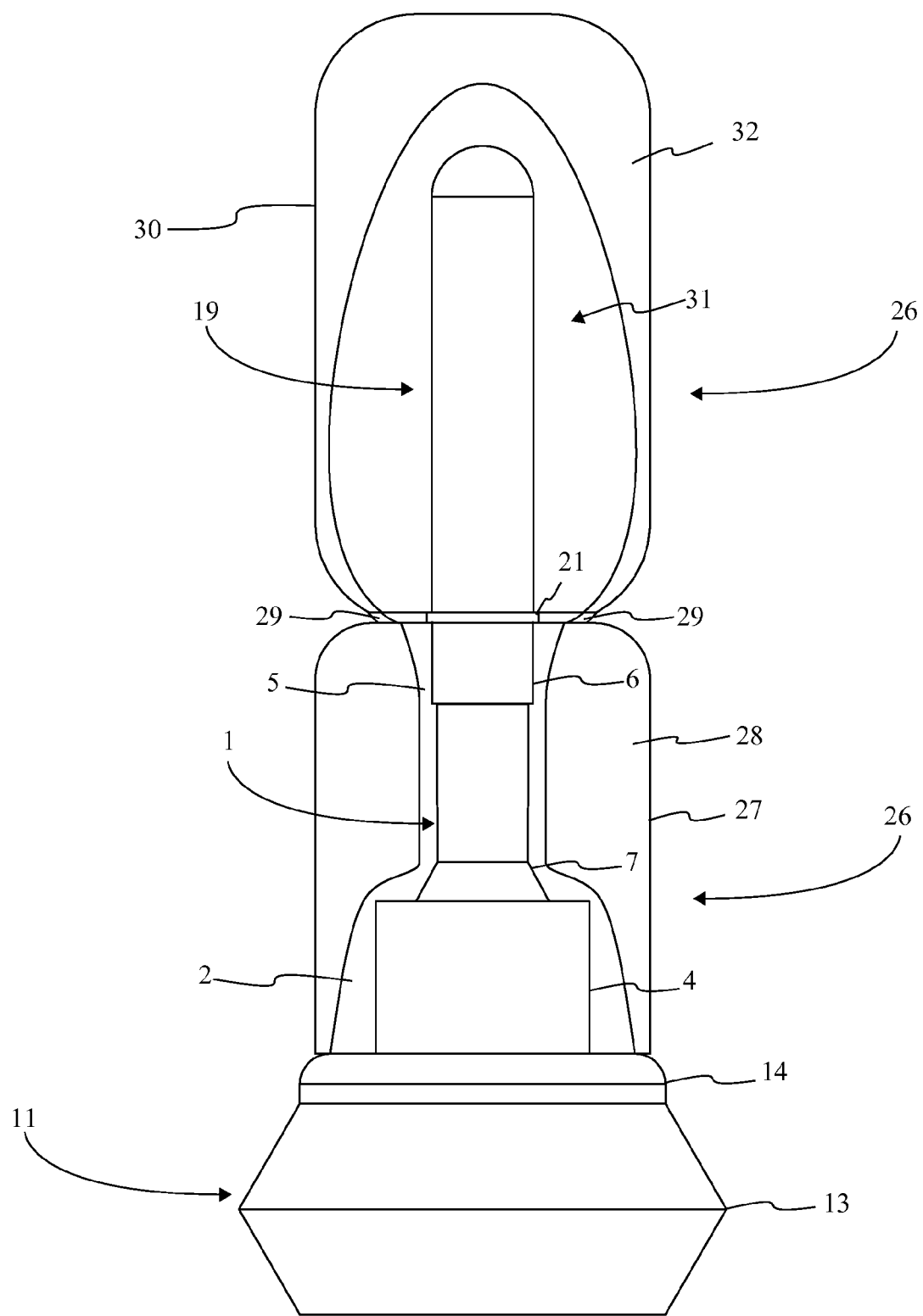
FIG. 2 is a front elevational view displaying the prefilled medical injection device as per the current embodiment of the present invention.
Figure 3:
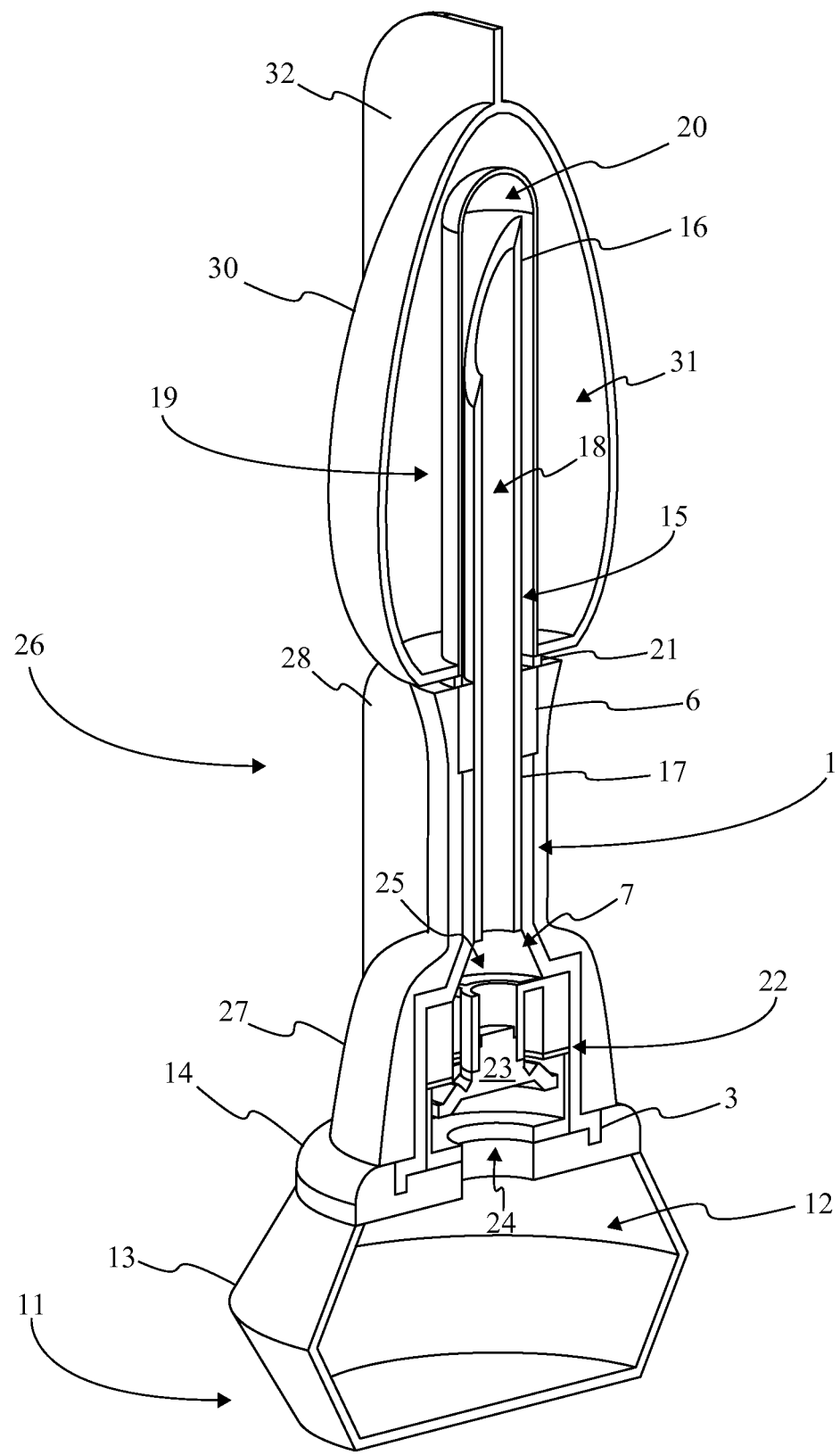
FIG. 3 is a cross sectional view displaying the internal component arrangement of the prefilled medical injection device as per the current embodiment of the present invention.

Referencing FIG. 1-3, the present invention is a prefilled medical injection device that is developed for use in the Blow Fill Seal (BFS) manufacturing process. The device accomplishes this through a particular component configuration that enables a compact and sterile design. In the current embodiment of the present invention, the prefilled medical injection device comprises an insert 1, a bellows 11, a valve 22, a needle assembly 15, a needle cap 19, and a parison layer 26. The insert 1 is a rigid component that functions as the attachment point for the bellows 11, the valve 22, the needle assembly 15, and the needle cap 19. The bellows 11 functions as a compressible vessel that holds a medication within its fluid chamber 12 until the flexible portion of the bellows 11 in compressed extruding the medication through the insert 1. The valve 22 is provided as a directionally biased fluid mechanism that prevents contamination of the medication. The needle assembly 15 is a fused attachment that permits the invention to inject the medication into a patient. The needle cap 19 functions as a safety mechanism that assists in preventing contamination as well as lowering the chances of accidental needle sticks. The parison layer 26 is a residual layer of material that is formed over the insert 1 and the needle cap 19 that hermetically seals the coupling between the insert 1 and the bellows 11.

Referencing FIG. 2-5, the components of the present invention are particularly arranged as a result of the specific requirements that allow the prefilled medical injection device to be produced using the BFS manufacturing process. The bellows 11 and the parison layer 26 are positioned in a manner that facilitates the attachment of the insert 1, the valve 22, the needle assembly 15, and the needle cap 19, during the BFS manufacturing process. The valve 22 is housed within the insert 1. The positioning of the valve 22 within the insert 1 is provided as means of securing and aligning the valve 22 with the bellows 11. The insert 1 is found coupled to the bellows 11. The parison layer 26 covers the engagement between the insert 1 and the bellows 11 creating a hermitic seal that protects the contents of the bellows 11 from contamination. The needle assembly 15 is fused to the insert 1 opposite the positioning of the bellows 11. The valve 22 is found positioned between the needle assembly 15 and the bellows 11. The bellows 11 and the needle assembly 15 are in fluid communication with each other by way of the valve 22. The valve 22 positioning between the bellows 11 and the needle assembly 15 provides a directionally biased flow of medication that reduces the risk of contamination. The needle assembly 15 is partly surrounded by the needle cap 19. The needle cap 19 encloses the needle assembly 15 in order to prevent contamination and accidental needle sticks. The parison layer 26 additionally encases the needle cap 19 serving as a secondary barrier that prevents the needle cap 19 from accidentally dislodging. It should be noted that in the current embodiment of the present invention, the bellows 11, the insert 1, the valve 22, the needle assembly 15, the needle cap 19, and the parison layer 26 are described with a non-specific alignment that provides the insert 1, the valve 22, and the needle assembly 15 as a conduit for fluid originating from the bellows 11. While the only requirement for the component distribution is to allow the insert 1, the valve 22, and the needle assembly 15 to function as a conduit, additional component distributions may require specific alignments for accommodating component engagements in the BFS manufacturing process.

Figure 5:
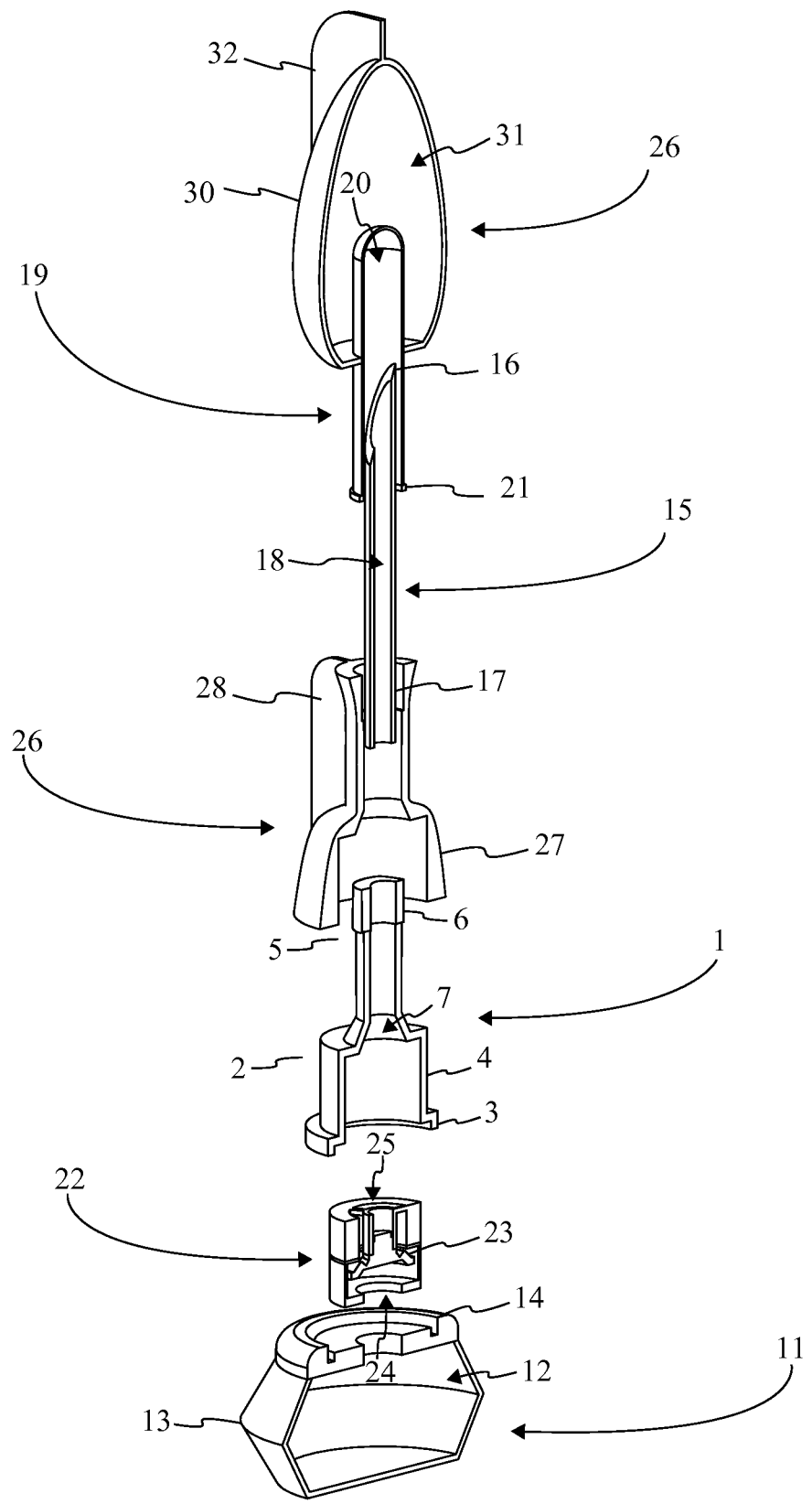
FIG. 5 is an expanded cross sectional view displaying the internal component distribution of the prefilled medical injection device as per the current embodiment of the present invention.
Figure 6:
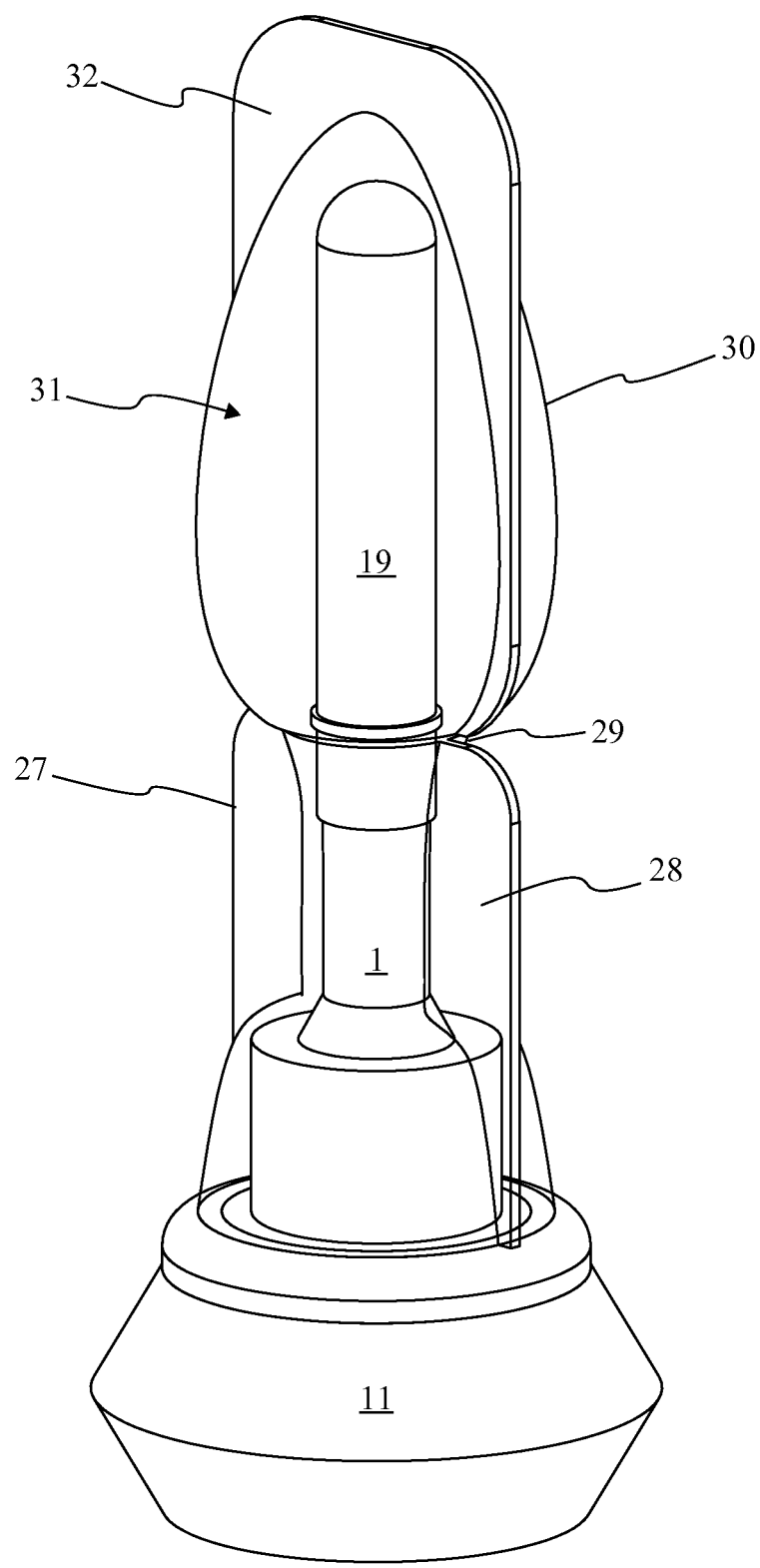
FIG. 6 is a perspective view displaying the frangible engagement between the needle cap cover and the insert layer in an intact state as per the current embodiment of the present invention.
Figure 7:
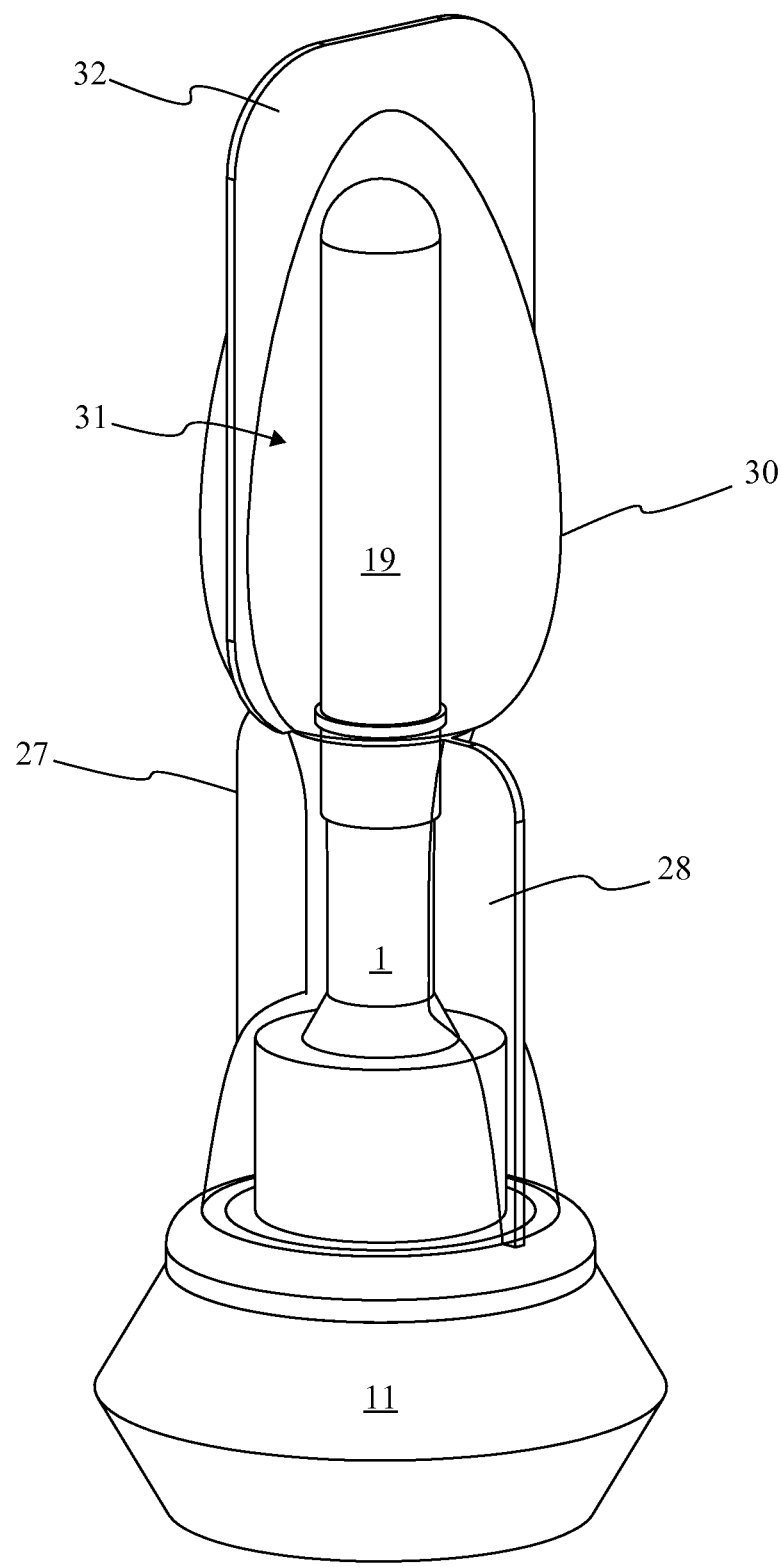
FIG. 7 is a perspective view displaying the frangible engagement between the needle cap cover and the insert layer being broken as per the current embodiment of the present invention.
Figure 8:
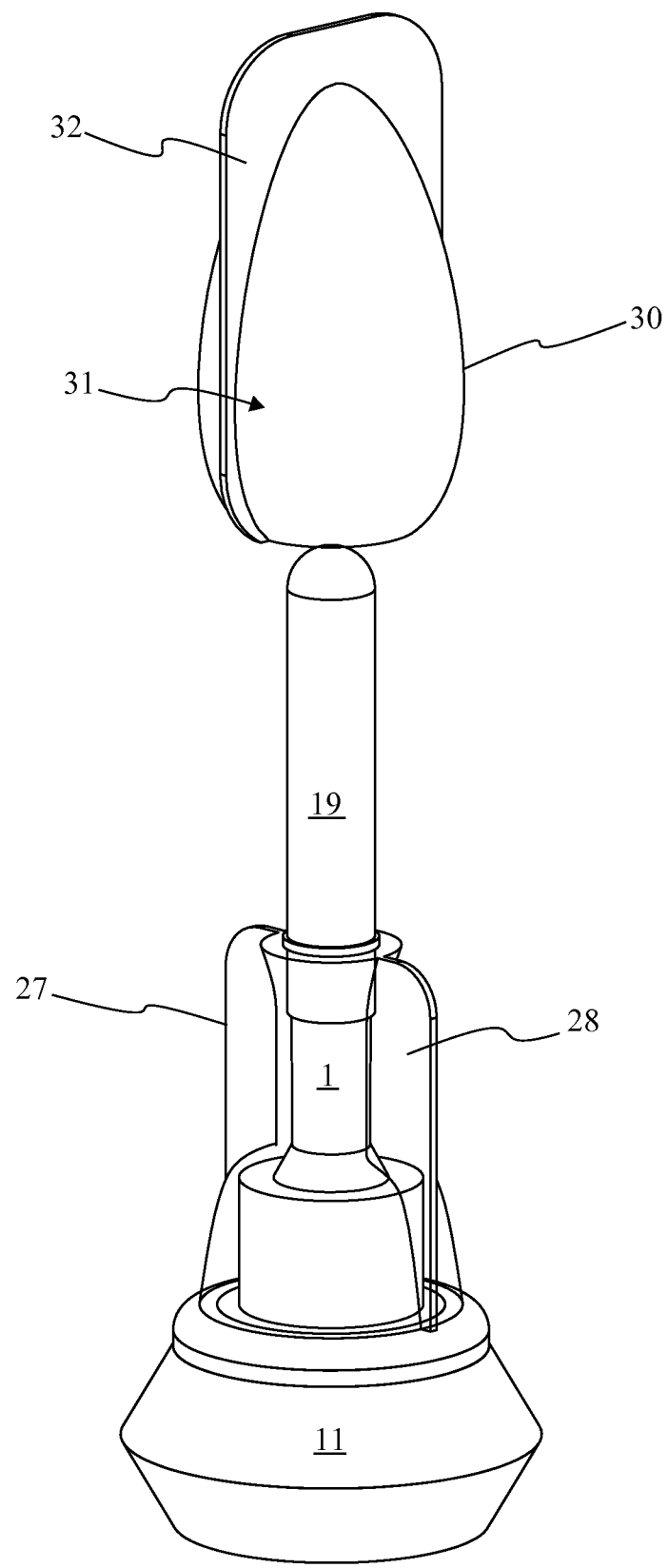
FIG. 8 is a perspective view displaying the needle cap cover separated from the insert layer following the breaking of the frangible engagement as per the current embodiment of the present invention.

Referencing FIG. 2 and FIG. 5, the insert 1 functions as the main body of the present invention that retains and aligns the bellows 11, the valve 22, and the needle assembly 15. The insert 1 is particularly formed to be asymmetrically balanced in order to favor a particular directionality when feeding the component through a feeding bowl during the BFS manufacturing process. In the current embodiment of the present invention, the insert 1 comprises a first end 2, a second end 5, and an insert fluid channel 7. The first end 2 and the second end 5 function as opposing regions of the insert 1 that aligns with the bellows 11 and the needle assembly 15 respectively. The insert fluid channel 7 is positioned between the valve mount 4 and the needle mount 6. The insert fluid channel 7 is provided as means of directing the extruded medication from the valve 22 into the needle assembly 15. The first end 2 is found opposite the second end 5 on along the length of the insert 1. The insert fluid channel 7 is found positioned between the first end 2 and the second end 5.

Referencing FIG. 2 and FIG. 5, the first end 2 of the insert 1 is found positioned adjacent to the bellows 11 while the second end 5 of the insert 1 is found positioned adjacent the needle assembly 15. In the current embodiment of the present invention, the first end 2 comprises a bellows mount 3 and a valve mount 4. The bellows mount 3 provides a mounting structure that particularly aligns the bellows 11 in a manner that permits fluid communication with the valve 22. It should be noted that the bellows mount 3 can be formed as a recessed or raised structure that compliments an engageable structure found on the bellows 11. The valve mount 4 is a formed section of the first end 2 that becomes coincident with the valve 22. The valve mount 4 securely holds the valve 22 within the insert 1 and aligns the valve 22 with bellows 11 and the needle assembly 15. It should be noted that the valve mount 4 allows for the insert 1 to be formed with the valve 22 prior to being fused with the bellows 11 during the BFS manufacturing process.

Referencing FIG. 2 and FIG. 5, the insert fluid channel 7 is found positioned between the valve mount 4 and the second end 5. The insert fluid channel 7 provides the directional flow of fluid extruded from the bellows 11 into the needle assembly 15. The insert fluid channel 7 is provided as a means of accounting for variations in diameter between the valve 22 and the needle assembly 15. It should be noted that the insert fluid channel 7 can be formed to funnel medication into the needle assembly 15 but can additionally function as an interstitial space that helps relieve pressure to the valve 22 during the extrusion of the fluid.

Referencing FIG. 2 and FIG. 5, the second end 5 is found opposite the first end 2 along the insert 1. The second end 5 is positioned adjacent to the needle assembly 15 and the needle cap 19. In the current embodiment of the present invention, the second end 5 comprises a needle mount 6. The needle mount 6 functions as the engagement point between the needle assembly 15 and the insert 1. The needle mount 6 is positioned adjacent to the insert fluid channel 7 opposite the valve mount 4. The needle mount 6 has a diameter that is roughly the same as the gauge of the needle assembly 15. The needle assembly 15 is fused to the needle mount 6 aligning the needle assembly 15 with the insert fluid channel 7. it should be noted that the while the needle mount 6 is described as a permanent engagement between the needle assembly 15 and the insert 1, in additional embodiments the needle mount 6 can function as a detachable engagement that provides the attachment of modular needle designs such as but not limited Luer lock engagements.

Referencing FIG. 1 and FIG. 2, the parison layer 26 is a residual component that is created with the formation of the bellows 11 during the BFS manufacturing process. During the BFS manufacturing process, the parison layer 26 is formed over the insert 1 and the needle cap 19. The parison layer 26 hermetically seals the coupling between the insert 1 and the bellows 11. In the current embodiment of the present invention, the parison layer 26 comprises an insert layer 27, a frangible engagement 29, and a needle cap cover 30. The insert layer 27 is formed to conform to the exterior of the insert 1. The insert layer 27 is formed in manner that increases the gripping surface near the insert 1. The insert layer 27 is fused to the bellows 11 opposite the frangible engagement 29. The frangible engagement 29 is found positioned between the insert layer 27 and the needle cap cover 30. The needle cap cover 30 and the insert layer 27 are detachably coupled by way of the frangible engagement 29. The needle cap cover 30 is found positioned over the needle cap 19. The needle cap cover 30 functions as a removable means of securing the needle cap 19 against the insert 1.

Figure 4:
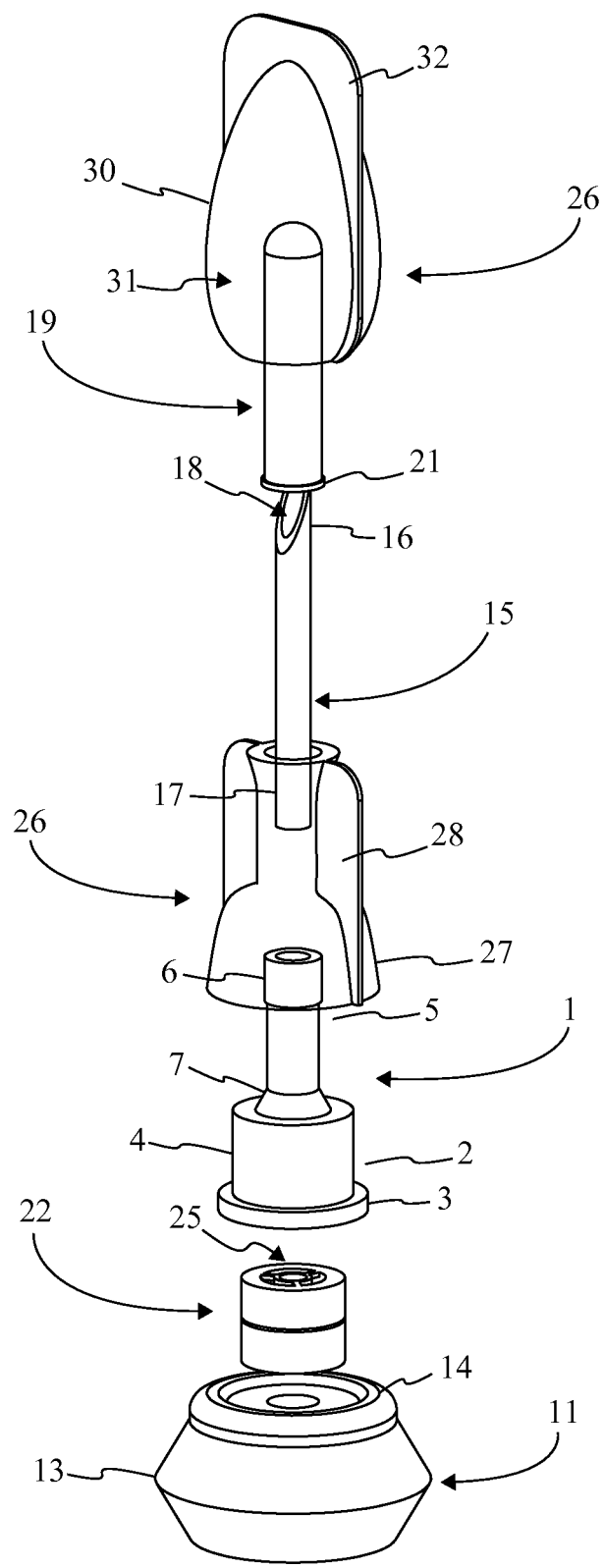
FIG. 4 is an expanded view displaying the component distribution of the prefilled medical injection device as per the current embodiment of the present invention.

Referencing FIG. 4 and FIG. 5, the insert layer 27 is the portion of the parison layer 26 that is molded to conform to the exterior of the insert 1. The insert layer 27 is fused with the bellows 11 as a result of being a residual of the formation of the bellows 11 during the BFS manufacturing process. The insert layer 27 covers the engagement between the insert 1 and the bellows 11 resulting in a hermetic seal between the insert 1 and the bellows 11 that reduces the risk of contamination. In the current embodiment of the present invention, the insert layer 27 comprises insert tabs 28. The insert tabs 28 provide a user with a more ergonomic gripping surface around the insert 1. The insert tabs 28 are found peripherally positioned flattened sections that bidirectionally extend outward from the insert layer 27. The insert tabs 28 are formed structures that arise following the attachment of the bellows 11 to the insert 1 through the BFS manufacturing process. During the BFS manufacturing process, the formation of the bellows 11 additionally creates a parison over tube. The insert 1, with the valve 22, the needle assembly 15, and the needle cap 19 attached, is then positioned within the parison over tube in order to engage the bellows 11. Following the proper engagement of the insert 1, the parison over tube is molded to conform to the exterior of the insert 1 and the needle cap 19. The molding of the parison over tube forms the parison layer 26. The parison layer 26 near around is then flattened and trimmed forming the insert is tabs. The insert tabs 28 increase the profile of the insert layer 27 allowing for facilitated manipulation by a user.

Referencing FIG. 5-8, the frangible engagement 29 is the portion of the parison layer 26 that permits a detachable engagement between the insert layer 27 and the needle cap cover 30. The frangible engagement 29 is formed when the parison layer 26 is flattened and trimmed. The trimming of the parison layer 26 creates a frangible webbing which functions as the frangible engagement 29 between the insert layer 27 and the needle cap cover 30. The needle cap cover 30 and the insert layer 27 are held together until the frangible engagement 29 is broken. The frangible engagement 29 is broken by rotating the needle cap cover 30 relative to the positioning of the insert layer 27.

The needle cap cover 30 is the portion of the parison layer 26 that is molded around the exterior of the needle cap 19. The needle cap cover 30 is a residual of the formation of the bellows 11 during the BFS manufacturing process. In the current embodiment of the present invention, the needle cap cover 30 comprises an inner chamber 31 and needle cap tabs 32. The inner chamber 31 of the needle cap cover 30 houses the needle cap 19. The needle cap tabs 32 provide an ergonomic gripping surface allowing a user to easily grip the needle cap cover 30. The needle cap tabs 32 are found peripherally positioned flattened sections that bidirectionally extend outward from the needle cap cover 30. The needle cap cover 30 is a formed structure that arises following the attachment of the bellows 11 to the insert 1 through the BFS manufacturing process. During the BFS manufacturing process, the formation of the bellows 11 additionally creates a parison over tube. The insert 1, with the valve 22, the needle assembly 15, and the needle cap 19 attached, is then positioned within the parison over tube in order to engage the bellows 11. Following the proper engagement of the insert 1, the parison over tube is molded to conform to the exterior of the insert 1 and the needle cap 19. The molding of the parison over tube forms a needle cap cover 30 around the needle cap 19. Following the formation of the needle cap cover 30, section of the needle cap cover 30 are flattened and trimmed forming the needle cap tabs 32. The needle cap tabs 32 increase the profile of the needle cap cover 30 allowing for facilitated manipulation by a user. It should be noted that in the current embodiment of the present invention, movement of the needle cap cover 30 occurs independently from the movement of the needle cap 19 due to the inner chamber 31 separating the needle cap cover 30 from the needle cap 19. In the current embodiment the needle cap cover 30 functions as means of reducing contamination but can additionally serve the purpose of a tamper evident seal. In additional embodiments of the present invention, the inner chamber 31 may be excluded or the needle cap cover 30 can be directly molded to the exterior of the needle cap 19 allowing the needle cap cover 30 to function as an extension of the needle cap 19. In this additional embodiment, movement applied to the needle cap cover 30 would translates to the needle cap 19 resulting in the needle cap 19 detaching from the insert 1 upon removal of the needle cap cover 30.

Referencing FIG. 3-5, the bellows 11 functions as a compressible vessel that contains a medication that is to be injected into a patient. The bellows 11 is coupled to the insert 1. In the current embodiment of the present invention the bellows 11 comprises a fluid chamber 12, a flexible body 13, and an insert mount 14. The fluid chamber 12 is the interior portion of the bellows 11 that is filled with a medication, vaccine, or pharmaceutical as well as combinations thereof for injection into patient. The flexible body 13 is the portion of the bellows 11 that is able to compress reducing the volume of the fluid chamber 12 and injecting the contents into patient. The insert mount 14 is the lower portion of the bellows 11 that provides an attachment point with the insert 1. The fluid chamber 12 is found surrounded by the flexible body 13. The insert mount 14 is positioned on the flexible body 13 adjacent the insert 1. The fluid chamber 12 is enclosed within the bellows 11 by the flexible body 13 and the insert mount 14. Upon compression of the flexible body 13, the volume of the fluid chamber 12 is decreased causing contents to be extruded across the valve 22 and into the needle assembly 15. The positioning of the insert mount 14 to the flexible body 13 provides a rim that enables a connection to the bellows mount 3 on the first end 2 of the insert 1.

Referencing FIG. 3-5, the fluid chamber 12 is the interior portion of the bellows 11 that contains the medication that is to be injected into a patient. The fluid chamber 12 is found positioned within the flexible body 13 and is enclosed by the engagement between the insert mount 14 and the bellows mount 3. The fluid chamber 12 contains a medication that is to be injected into a patient but additionally includes an inert gas that fills a head space. The head space is provided as an inert gas that fills the remaining volume of the fluid chamber 12. Upon compression of the fluid chamber 12 by the flexible body 13, the inert gas in the head space forces the entire dosage of the medication through the valve 22 and into the needle assembly 15.

Referencing FIG. 3-5, the insert mount 14 functions as the complementary engagement structure that couples the insert 1 to the bellows 11. The insert mount 14 is a bounding rim that partly encloses the fluid chamber 12 within the flexible body 13. The insert mount 14 forms a partial opening allowing access to the fluid chamber 12. Through the particular positioning of the insert mount 14 and the flexible body 13 relative to the bellows mount 3 and the valve 22, the fluid chamber 12 is able to direct all medication across the valve 22. It should be noted that the insert mount 14 can be formed as a recessed or raised structure that compliments the bellows mount 3 of the first end 2. Furthermore it should be noted that while the insert mount 14 and the bellows mount 3 are coupled together, their engagement is provided mostly for structural support.

Referencing FIG. 3-5, the valve 22 is the directionally biased component that is securely retained to the valve mount 4 within the first end 2. The valve 22 is found positioned between the fluid chamber 12 and the insert fluid channel 7. It should be noted that the valve 22 could be formed into the insert 1 resulting in the same relative positioning to the bellows 11 and the needle assembly 15, eliminating the valve mount 4 as a redundant component. In the current embodiment of the present invention, the valve 22 comprises a first opening 24, a second opening 25, and a one way mechanism 23. The first opening 24 is provided as an intake for the medication to flow into the valve 22. The one way mechanism 23 is the directionally biased means by which the medication is permitted to flow in a single direction after entering the valve 22. The second opening 25 in the exhaust opening through which the medication flows out of after being directed through the one way mechanism 23. It should be noted that the one way mechanism 23 may be provided by a plurality of valve 22 mechanism that are small enough to fit within the insert 1. These valve 22 mechanisms include but are not limited to Bellville valve 22s, ball valve 22s, and umbrella valve 22s. It should be noted that through the incorporation of the one way valve 22 the present invention is essentially a single use device that can be discarded in a sharps disposal box following administration of the medication.

Referencing FIG. 3-5, the first opening 24 is in fluid communication with the second opening 25 by way of the one way mechanism 23 the first opening 24 is the intake opening that allows medication from the fluid chamber 12 to enter the valve 22. Within the valve 22 the one way mechanism 23 functions as the main component that permits the medication to flow out of the second opening 25 and through the insert fluid channel 7. The one way mechanism 23 is provided as means of preventing contamination of the medication within the fluid chamber 12. The one way mechanism 23 accomplishes this by prevention aspiration of contaminants cause by negative pressure forming in the fluid chamber 12 as a result of environmental effects or volume changes in to the bellows 11. In the current embodiment of the present invention the one way mechanism 23 is able to resists at least a pound per square inch PSI change within the fluid chamber 12. The second opening 25 is provided as the exhaust opening through which the medication passes through on its way to the insert fluid channel 7.

Referencing FIG. 3-5, the needle assembly 15 is the component that allows the medication to be injected into a patient. The needle assembly 15 is positioned adjacent to the second end 5 and is fused to the needle mount 6. In the current embodiment of the present invention the needle assembly 15 comprises a sharp end 16, a mounted end 17, and a needle fluid channel 18. The sharp end 16 of the needle assembly 15 is the terminal end that is inserted into a patient. The mounted end 17 is the portion that is fused to the needle mount 6 of the second end 5. The needle fluid channel 18 is a centrally positioned passage that allows the medication from the bellows 11 to be injected into the patient. The needle fluid channel 18 is centrally positioned and traverses both the mounted end 17 and the sharp end 16.

Referencing FIG. 3-5, the sharp end 16 of the needle assembly 15 is the sticking end. The sharp end 16 is terminally positioned opposite to the mounted end 17. It should be noted that although the sharp end 16 is described as being used for injecting into a patient, it could simply be the extrusion point of the medication. By allowing the sharp end 16 to function as the extrusion point of the medication, the prefilled medical injection can be used to inject medication into an Intravenous Fluid bag rather than directly into the patient.

Referencing FIG. 3-5, the mounted end 17 of the needle assembly 15 is the portion of the needle assembly 15 that is fused to the needle mount 6. The mounted end 17 of the needle fits within the needle mount 6 in order to fuse with the second end 5 of the insert 1. It should be noted that the mounted end 17 of needle assembly 15 describes the gauge of the needle itself, as well as any structural component that could be used to secure the needle assembly 15 to the needle mount 6. It should be noted that mounted end 17 can also be provided solely as the needle body. In this version the gauge of the needle would be measured to fit the needle mount 6. In an additional embodiment of the present invention, the mounted end 17 would comprise a detachable mounting mechanism that would allow the needle assembly 15 to function as part of modular system. In this additional embodiment the mounted end 17 could be accomplished by a Luer lock needle connection.

Referencing FIG. 3-5, the needle fluid channel 18 is found in fluid communication with the insert fluid channel 7. The needle fluid channel 18 is found traversing through the mounted end 17 and the fused end. The needle fluid channel 18 mount is of a particular diameter that is dependent on the gauge of the needle assembly 15. It should be noted that the gauge of the needle assembly 15 can be accommodated to function with a plurality of injection routes that include but are not limited to intramuscular, intravenous, and subcutaneous injections.

Referencing FIG. 3-5, the needle cap 19 functions as a safety mechanism that assists in preventing contamination as well as lowers the chances of accidental needle sticks. The needle cap 19 accomplishes this by encasing part of the needle assembly 15. The needle cap 19 is detachably coupled to the second end 5 of the insert 1. In the current embodiment of the present invention, the needle cap 19 comprises a needle cavity 20 and a flange 21. The needle cavity 20 is the interior portion of the needle cap 19 that is contains the sharp end 16 of the needle assembly 15. The flange 21 is the portion of the needle cap 19 that is traversed by the sharp end 16. It should be noted that the needle cap 19 would be positioned over the needle following or concurrently with the attachment of the needle assembly 15 to the insert 1 in the BFS manufacturing process.

Referencing FIG. 3-5, the needle cavity 20 is the internal portion of the needle cap 19 that encloses the sharp end 16 of the needle assembly 15. The needle cavity 20 functions as an internal space. The needle cap 19 itself sleeves the sharp end 16 of the needle assembly 15 wherein the sharp end 16 resides within the needle cavity 20. The needle cavity 20 is provided as a sterile enclosed space. The needle cavity 20 additionally accounts for accidental extrusion of medication into the needle cap 19. The needle cavity 20 is provided with an internal volume that can accommodate at least some volume of medication and the sharp end 16 of the needle assembly 15.

Referencing FIG. 3-5, the flange 21 is found coincident with the second end 5 of the insert 1. The flange 21 is traversed by the sharp end 16 of the needle assembly 15 in order to become coincident with the needle cavity 20. The flange 21 additionally functions as mount for the needle cap 19 with the second end 5 of the insert 1.

In an embodiment of the invention the bellows 11 is constructed using the Low-density polyethylene (LDPE). The low density polyethylene is selected due to its inherent benefits associated in the BFS manufacturing process. LDPE is a strong light weight polymer with some elasticity that makes it a perfect material for use as a bellows 11. Furthermore the election of the LDPE provides improved adhesion to a high density polyethylene constructed insert 1.

In an embodiment of the invention the bellows 11 is constructed using Polypropylene (PP). The polypropylene is selected due to its benefits in the BFS manufacturing process. Polypropylene is a cost effective and is more flexible than LDPE.

In an embodiment of the invention the insert 1 is constructed of Polypropylene (PP). The polypropylene is selected due to its benefits in the BFS manufacturing process. Polypropylene is a cost effective and is more flexible than LDPE. The polypropylene can fuse to the LDPE or PP constructed bellows 11 with considerable ease resulting in a strong engagement between components.

In an embodiment of the invention the insert 1 is constructed of Low density polyethylene. The low density polyethylene is selected for use in the construction of the insert 1, due to its ability to form a stronger engagement with and LDPE bellows 11.

Although the invention has been explained in relation to its preferred embodiment, it is to be understood that many other possible modifications and variations can be made without departing from the spirit and scope of the invention as hereinafter claimed.

The invention claimed is:

1. An integrated injection device with pre-packaged medication, comprising:
   a compressible, hermetically-sealed medication compartment at least partially filled with the pre-packaged medication;
   a needle;
   a pressure-actuated valve in selectable fluid communication between the compartment and the needle wherein, upon compression of the compartment, the pre-packaged medication in caused to flow from the compartment, through the valve, and then through the needle;
   a balanced insert body that retains and aligns the compartment, the valve and the needle, ensuring that they are in selectable fluid communication;
   a frangible web at least partially encapsulating the injection device, wherein upon breaking the web package, at least a tip of the needle is exposed; and
   the valve resisting a backflow of any fluid from the needle back into the compartment.

2. The integrated injection device if claim 1, wherein the insert body comprises an insert fluid channel shaped to account for variation in diameters in radial direction between the valve and the needle.

3. The integrated injection device if claim 1, wherein the device is manufactured using a blow-fill-seal manufacturing process.

4. The integrated injection device if claim 1, wherein the compartment comprises a translucent low-density polyethylene.

5. The integrated injection device if claim 1, wherein the compartment includes an inert gas in addition to the medication, and the inert gas facilitates removal of the medication from the compartment upon compression of the compartment.

6. The integrated injection device if claim 1, wherein the needle comprises either an integrated or Luer-lok threaded needle.

7. The integrated injection device if claim 1, wherein the medication is inserted either into a patient or into an intravenous fluid bag.

8. A process for forming an integrated injection device with pre-packaged medication as claimed in claim 1, comprising the steps of:
   forming a hot, tubular-shaped parison into a mold having at least a first compartment;
   at least partially filling the first compartment with a dose of the medication; and
   positioning a premade insert assembly within the mold in order to engage the compartment.

9. The process of claim 8, further comprising the step, after the positioning step, of hermetically sealing a coupling between the insert assembly and the first compartment.

10. The process of claim 8, further comprising the step of shaping the mold to conform to the exterior of the insert assembly.

11. The process of claim 8, wherein the premade insert assembly comprises at least a valve and a needle.

12. The process of claim 8, wherein each of the steps occurs continuously, substantially without human intervention, in a sterile enclosed area inside a machine.

13. The process of claim 8, wherein following the introduction of the premade insert assembly into the mold, a frangible web at least partially encapsulates the injection device.

14. The blow-fill-seal method of claim 8, wherein an electronic fill system is utilized to deliver a precise does of the medication into the first compartment.

* * * * *